( 12 ) United States Patent
Hodges et al.

(10) Patent No.: US 8,883,190 B2
(45) Date of Patent: *Nov. 11, 2014

(54) UROLOGIC DEVICES INCORPORATING COLLAGEN INHIBITORS

(75) Inventors: Steve J. Hodges, Winston-Salem, NC (US); Anthony Atala, Winston-Salem, NC (US); James J. Yoo, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 385 days.

This patent is subject to a terminal disclaimer.

(21) Appl. No.: 11/948,335

(22) Filed: Nov. 30, 2007

(65) Prior Publication Data

US 2008/0133027 A1 Jun. 5, 2008

Related U.S. Application Data

(60) Provisional application No. 60/868,217, filed on Dec. 1, 2006.

(51) Int. Cl.
*A61F 6/06* (2006.01)
*A61K 9/70* (2006.01)
(Continued)

(52) U.S. Cl.
CPC .............. *A61K 9/7007* (2013.01); *A61K 9/0034* (2013.01); *A61F 2/82* (2013.01); *A61F 2/042* (2013.01); *A61L 15/44* (2013.01); *A61L 27/54* (2013.01); *A61L 29/16* (2013.01); *A61L 31/16* (2013.01); *A61L 2300/432* (2013.01); *A61B 17/04* (2013.01); *A61L 17/00* (2013.01); *Y10S 606/907* (2013.01); *A61K 9/146* (2013.01); *A61K 31/517* (2013.01)
USPC .......................................... 424/430; 606/907

(58) Field of Classification Search
CPC ......... A61K 9/0034; A61F 2/04; A61F 2/042; A61F 2/82; A61L 27/54; A61L 31/00
See application file for complete search history.

(56) References Cited

U.S. PATENT DOCUMENTS 4,291,687 A 9/1981 Sinnreich
4,485,088 A 11/1984 Chvapil
(Continued)

FOREIGN PATENT DOCUMENTS

CA 2603081 9/2013
WO WO 98/23244 6/1998
(Continued)

OTHER PUBLICATIONS

Bosher LH et al. The pathology of experimentally produced lye burns and strictures of the esophagus. The Journal of Thoracic Surgery. 1951: 483-489.

(Continued)

*Primary Examiner* — Bethany Barham
(74) *Attorney, Agent, or Firm* — Myers Bigel Sibley & Sajovec, P.A.

(57) ABSTRACT

Provided herein are implantable or insertable biomedical devices comprising a substrate and a collagen inhibitor on or in said substrate, and methods of treatment using the same. In some embodiments, the device is a urethral, ureteral, or nephroureteral catheter or stent. Kits comprising the same are also provided.

18 Claims, 3 Drawing Sheets

(51) Int. Cl.
*A61K 9/00* (2006.01)
*A61F 2/82* (2013.01)
*A61F 2/04* (2013.01)
*A61L 15/44* (2006.01)
*A61L 27/54* (2006.01)
*A61L 29/16* (2006.01)
*A61L 31/16* (2006.01)
*A61B 17/04* (2006.01)
*A61L 17/00* (2006.01)
*A61K 9/14* (2006.01)
*A61K 31/517* (2006.01)

(56) References Cited

U.S. PATENT DOCUMENTS

| | | | |
|---|---|---|---|
| 5,092,841 A | 3/1992 | Spears | |
| 5,263,927 A | 11/1993 | Shlain | |
| 5,385,935 A | 1/1995 | Tamai et al. | |
| 5,449,678 A * | 9/1995 | Pines et al. | 514/266.22 |
| 5,564,439 A | 10/1996 | Picha | |
| 5,685,860 A | 11/1997 | Chang et al. | |
| 5,723,448 A | 3/1998 | Gross et al. | |
| 5,755,788 A * | 5/1998 | Strauss | 623/1.1 |
| 5,852,024 A | 12/1998 | Pines et al. | |
| 6,028,078 A | 2/2000 | Hausheer et al. | |
| 6,046,340 A | 4/2000 | Seguin et al. | |
| 6,063,396 A | 5/2000 | Kelleher | |
| 6,090,814 A | 7/2000 | Nagler et al. | |
| 6,159,488 A | 12/2000 | Nagler et al. | |
| 6,224,630 B1 | 5/2001 | Bao et al. | |
| 6,239,177 B1 | 5/2001 | Mori et al. | |
| 6,281,262 B1 | 8/2001 | Shikinami | |
| 6,328,994 B1 | 12/2001 | Shimizu et al. | |
| 6,376,543 B1 | 4/2002 | Isaji et al. | |
| 6,420,371 B1 | 7/2002 | Pines et al. | |
| 6,638,917 B1 | 10/2003 | Li et al. | |
| 7,025,753 B2 | 4/2006 | Reever | |
| 7,097,857 B2 | 8/2006 | Tracy et al. | |
| 7,135,197 B2 | 11/2006 | Pena et al. | |
| 7,189,410 B1 | 3/2007 | Drohan et al. | |
| 2003/0108588 A1 | 6/2003 | Chen et al. | |
| 2003/0144727 A1 | 7/2003 | Rosenthal et al. | |
| 2004/0043052 A1* | 3/2004 | Hunter et al. | 424/426 |
| 2005/0038498 A1* | 2/2005 | Dubrow et al. | 623/1.15 |
| 2005/0187609 A1 | 8/2005 | Brar et al. | |
| 2005/0208095 A1 | 9/2005 | Hunter et al. | |
| 2005/0220882 A1 | 10/2005 | Pritchard et al. | |
| 2005/0234538 A1 | 10/2005 | Litvack et al. | |
| 2006/0020331 A1 | 1/2006 | Bates et al. | |
| 2006/0147492 A1 | 7/2006 | Hunter et al. | |
| 2006/0177480 A1 | 8/2006 | Sung et al. | |
| 2006/0204537 A1 | 9/2006 | Ratner et al. | |
| 2006/0229711 A1 | 10/2006 | Yan et al. | |
| 2006/0293351 A1 | 12/2006 | Pines et al. | |
| 2007/0038291 A1 | 2/2007 | Case et al. | |
| 2007/0048351 A1 | 3/2007 | Lunn | |
| 2007/0142339 A1* | 6/2007 | Whitehouse et al. | 514/167 |
| 2007/0148205 A1 | 6/2007 | Whitehouse et al. | |
| 2007/0160640 A1 | 7/2007 | Jang et al. | |
| 2007/0299409 A1 | 12/2007 | Whitbourne et al. | |
| 2008/0095819 A1 | 4/2008 | Gourdie et al. | |
| 2008/0097580 A1 | 4/2008 | Dave | |
| 2008/0116106 A1* | 5/2008 | Lampropoulos et al. | 206/570 |
| 2009/0171317 A1* | 7/2009 | Versi | 604/517 |
| 2009/0226500 A1 | 9/2009 | Avelar et al. | |
| 2010/0021519 A1 | 1/2010 | Shenoy | |

FOREIGN PATENT DOCUMENTS

| | | |
|---|---|---|
| WO | WO 02/36054 A1 | 5/2002 |
| WO | WO 02/087586 A1 | 11/2002 |
| WO | WO 2005/079703 A1 | 9/2005 |
| WO | WO 2005-112999 A2 | 12/2005 |
| WO | WO 2005-113031 A2 | 12/2005 |
| WO | WO 2006/107957 A2 | 10/2006 |
| WO | WO 2006/116989 A2 | 11/2006 |
| WO | WO 2007-084396 A2 | 7/2007 |

OTHER PUBLICATIONS

Burford TH et al. Caustic burns of the esophagus and their surgical management: a clinico-experimental correlation. Annals of Surgery. Sep. 1953; 139(3): 453-460.

McBride W et al. Restenosis after successful coronary angioplasty. The New England Journal of Medicine. Jun. 30, 1988; 318(26): 1734-1737.

Lindner V et al. Role of basic fibroblast growth factor in vascular lesion formation. Circulation Research. 1991; 68(1): 106-113.

Baskin LS et al. Biochemical characterization and quantitation of the collagenous components of urethral stricture tissue. The Journal of Urology. Aug. 1993; 150(2 Pt 2): 642-7 Abstract only.

Granot I et al. Halofuginone: an inhibitor of type I synthesis. Biochimica et Biophysica Acta. Feb. 13, 1993; 1156(2): 107-112 Abstract only.

Choi ET et al. Halofuginone, a specific collagen type I inhibitor, reduces anastomotic intimal hyperplasia. Arch Surg. Jun. 1995; 130(6): 257-261.

Nyska M et al. Topically applied halofuginone, an inhibitor of collagen type I transcription, reduces peritendinous fibrous adhesions following surgery. Connective Tissue Research. 1996; 34(2): 97-103 Abstract only.

Nagler A et al. Inhibition of collagen synthesis, smooth muscle cell proliferation, and injury-induced intimal hyperplasia by halofuginone. Arteriosclerosis, Thrombosis, and Vascular Biology. Jan. 1997;17(1):194-202 Abstract only.

Liu K et al. Halofuginone inhibits neointimal formation of cultured rat aorta in a concentration-dependent fashion in vitro. Heart Vessels. 1998; 13(1): 18-23 Abstract only.

Nagler A et al. The effect of halofuginone, an inhibitor of collagen type I synthesis, on urethral stricture formation: in vivo and in vitro study in a rat model. The Journal of Urology; Nov. 2000; 164(5): 1776-1780.

Regar E et al. Stent development and local drug delivery. British Medical Bulletin. 2001; 59: 227-48.

Da Silva FA et al. Extracellular matrix changes in urethral stricture disease. The Journal of Urology. Aug. 2002; 168: 805-807.

Finn AV et al. A novel rat model of carotid artery stenting for the understanding of restenosis in metabolic diseases. Journal of Vascular Research. 2002; 39: 414-426 (Marked copy).

Shargal Y et al. Inhibition of anastomotic intimal hyperplasia by a synthetic nonsulphated heparin-mimicking compound. Exp Clin Cardiol. Autumn 2002; 7(2/3): 73-79.

Arbell D et al. Prevention of esophageal strictures in a caustic burn model using halofuginone, an inhibitor of collagen type I synthesis. Laryngoscope 2005; 115(9): 1632-5 Abstract only.

Ferguson DD. Evaluation and management of benign esophageal strictures. Diseases of the Esophagus. 2005; 18: 359-364.

Mitra AK and Agrawal DK. In stent restenosis: bane of the stent era. J Clin Pathol. 2006; 59: 232-239.

Tierney W et al. Enteral stents. Technology Evaluation Report. Gastrointestinal Endoscopy. 2006; 63(7): 920-926.

Kopecki Z et al. Collagen loss and impaired wound healing is associated with c-Myb deficiency. Journal of Pathology. 2007; 211: 351-361.

Maluenda G et al. A critical appraisal of the safety and efficacy of drug-eluting stents. Clinical Pharmacology & Therapeutics. May 2009; 85(5): 474-480.

Leigh Perkins LE. Preclinical models of restenosis and their application in the evaluation of drug-eluting stent systems. Veterinary Pathology. Jan. 2010; 47(1): 58-76.

Schembre D. Advances in esophageal stenting: the evolution of fully covered stents for malignant and benign disease. Adv Ther. 2010: 27(7): 413-425.

Sharma P. et al. Role of esophageal stents in benign and malignant diseases. The American Journal of Gastroenterology. Feb. 2010; 105: 258-273.

Coronary stent. Wikipedia. Retrieved Nov. 13, 2010: 1 p.

(56) References Cited

OTHER PUBLICATIONS

Foley catheter. Wikipedia. Retrieved Nov. 13, 2010: 3 pp.
Ureteric stent. Wikipedia. Retrieved Nov. 13, 2010: 3 pp.
Wound healing. Wikipedia. Retrieved Nov. 13, 2010: 15 pp.
Stenosis. Wikipedia. Retrieved Jan. 18, 2011: 2 pp.
RD 476079. Drug delivering device, e.g. drug-delivery stent, for treating vascular disease, comprises topcoat make from material that is biocompatible and biostable and delivering drug, where gastric or enteric coating is used for topcoat. Dec. 2003. 2 pp.
Cavalcanti AG et al. A morphometric analysis of bulbar urethral strictures. Reconstructive Urology. 2007;100:397-402.
Tabassi KT et al. Triamcinolone injection following internal urethrotomy for treatment of urethral stricture. Urology Journal. 2011; 8(2): 132-136.
Mazdak H et al. Effect of mitomycin G on anterior urethral stricture recurrence after internal urethrotomy. European Urology. 2007; 51: 1089-1092.
Mucous Membrane. Wikipedia. 4 pp, retrieved Dec. 23, 2011.
Urine. Wikipedia. 11 pp, retrieved Feb. 27, 2012.
Halocur. Committee for Veterinary Medicinal Products, European Public Assessment Report. The European Agency for the Evaluation of Medicinal Products Evaluation of Medicines for Veterinary Use. 1999; 61 pp.
Putnam DF. Composition and concentrative properties of human urine. NASA Contractor Report. Jul. 1971: 1-107.
Krane LS et al. Halofuginone-coated urethral catheters prevent periurethral spongiofibrosis in a rat model of urethral injury. Journal of Endourology. Jan. 2011; 25(1): 107-112.
"Palmoplantar pustulosis" from DermNetNZ pp. 1-2, retrieved Sep. 23, 2011.
Supplementary European Search Report, EP 07862365, mailed Apr. 28, 2011.
Nehls MC et al. Mithramycin Selectively inhibits collagen-β1(I) gene expression in human fibroblast. J. Clin. Invest. (Dec. 1993) 92: 2916-2921.
Retraction of: [Nehls MC et al. Mithramycin Selectively inhibits collagen-β1(I) gene expression in human fibroblast. J. Clin. Invest. (Dec. 1993) 92: 2916-2921] J. Clin. Invest. (Oct. 2003) 112(8): 1265.
Yamada H. et al. Tranilast, a selective inhibitor of collagen synthesis in human skin fibroblasts. J. Biochem. (Oct. 1994) 116(4): 892-897, Abstract only.
Chen S-J et al. Mithramycin inhibits myointimal proliferation after balloon injury of the rat carotid artery in vivo. Circulation (Nov. 1994) 90(5): 2468-73.
Nagler A. et al. Halofuginone—an inhibitor of collagen type I synthesis—prevents postoperative formation of abdominal adhesions. Annals of Surgery (1998) 227(4): 575-582.
Fishbein I et al. Local delivery of mithramycin restores vascular reactivity and inhibits neointimal formation in injured arteries and vascular grafts. Journal of Controlled Release (2001) 77: 167-181.
Sandorfi N. et al. Inhibition of collagen gene expression in systemic sclerosis dermal fibroblasts by mithramycin. Ann Rheum Dis (2005) 64: 1685-1691.
Tanaka et al. Newly developed biodegradable stents for benign gastrointestinal tract stenosis: a preliminary clinical trial. Digestion (Mar. 6, 2006) 74: 199-205.
FDA Oncology Tools Product Label Details in Conventional Order for plicamycin, mithramycin. U.S. Food and Drug Administration. Supplemental No. 050109, 8 pp, May 30, 2008.
International Search Report and Written Opinion, PCT/US07/024615, mailed Apr. 3, 2008.

\* cited by examiner

UROLOGIC DEVICES INCORPORATING COLLAGEN INHIBITORS

RELATED APPLICATIONS

This application claims the benefit of U.S. Provisional Patent Application Ser. No. 60/868,217, filed Dec. 1, 2006, the disclosure of which is incorporated by reference herein in its entirety.

FIELD OF THE INVENTION

The present invention concerns medical devices, including implantable devices such as catheters and stents.

BACKGROUND OF THE INVENTION

Luminal strictures, such as urethral or ureteral strictures, represent a vexing problem for urologists. Urethral strictures result from spongiofibrosis, most of which is composed of type I collagen, and are due to the imbalance of collagen formation and destruction following urethral injury (Baskin et al. J. Urol. 1993. August 150 (2 Pt 2): 642-7). Urethral strictures are commonly treated with dilation and/or incision followed by stenting, but such techniques have suffered from high failure rates. The use of pharmacologic agents to prevent stricture formation (e.g. MMC, steroids, colchicine) have improved treatment results only marginally.

Short urethral strictures are typically treated with a direct visual internal urethrotomy (DVIU), or incision of the stricture, followed by catheter stenting for approximately 4 days, in hopes that the new scar will heal around the stent, leaving a large caliber urethra. Unfortunately, wound healing cannot be well controlled, and the new incision heals via the deposition of type-I collagen, which may contract, causing a high rate of stricture recurrence.

Orally administered and locally injected haloflignone has been shown to prevent collagen deposition and stricture formation in the ureter and urethra in animal models of urologic strictures (Turk et al. J. Endourol. 2000 March; 14(2):145-7; Nagler et al. J. Urol. 2000 November; 164(5):1776-80; Jaidane et al. J. Urol. 2003 November; 170(5):2049-52). Oral doses of up to 3.5 mg/day were administered to patients with solid tumors with minimal ill effects (Jianng et al. Antimicrob Agents Chemother. 2005 March; 49(3):1169-76).

However, oral administration or administration by injection is not ideal. There is need for new approaches to alleviate urethral strictures and other problems associated with medical interventions.

SUMMARY OF THE INVENTION

Provided herein are implantable or insertable biomedical devices comprising a substrate and a collagen inhibitor on or in said substrate. In some embodiments, the device is a urethral, ureteral, or nephroureteral catheter or stent. In some embodiments, the substrate includes a material selected from the group consisting of vinyl, polyethylene, poly(vinyl chloride) (PVC), ethylene vinyl acetate (EVA), silicone, latex, and polypropylene. In some embodiments, the collagen inhibitor is selected from the group consisting of: mithramycin, mitomycin-c, tranilast, halofuginone and analogs thereof.

Methods of treating urethral or ureteral strictures in a subject in need thereof are also provided, including topically administering a collagen inhibitor in an amount effective to treat the urethral strictures. In some embodiments, the administering step is carried out by stenting with a catheter (e.g., a silicone catheter) coated with the collagen inhibitor. In some embodiments, the collagen inhibitor is selected from the group consisting of: mithramycin, mitomycin-c, tranilast, halofuginone and analogs thereof.

Kits including the implantable or insertable biomedical devices are also provided.

The present invention is explained in greater detail in the specification set forth below.

DETAILED DESCRIPTION OF THE PREFERRED EMBODIMENTS

Figure 1:
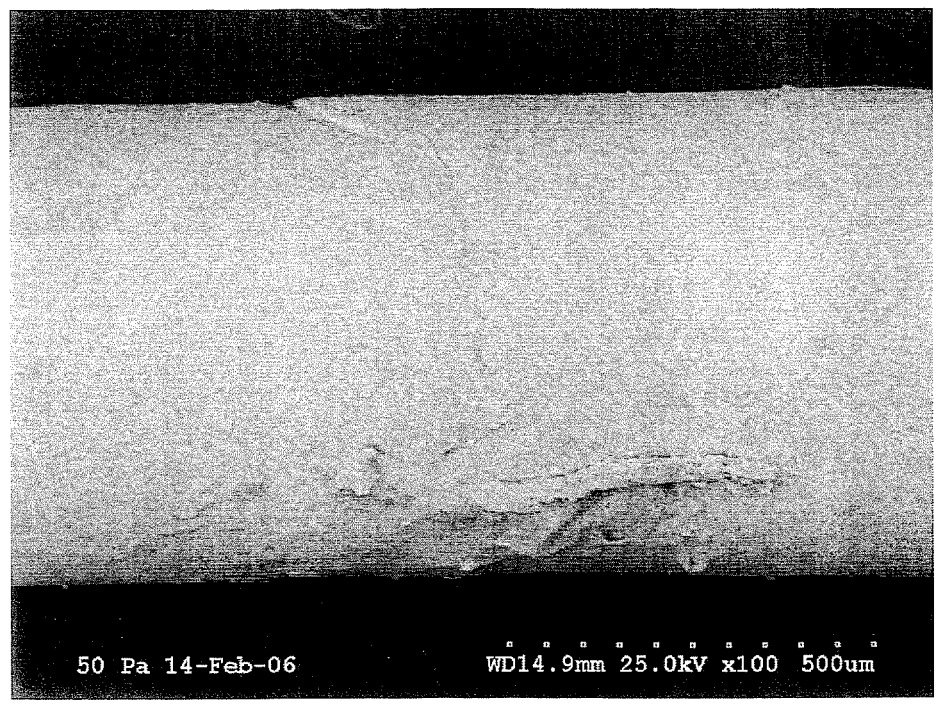
FIG. 1. SEM image of HFBr coating on silicone urethral stent used in rat model.

The disclosures of all United States Patent references cited herein are to be incorporated by reference herein as if fully set forth.

Healing through the deposition of scar (fibrous) tissue is the normal response to injury. In humans, the wound healing response is divided into three phases: inflammation, fibroplasias and maturation. The steps of the process overlap broadly and are best understood as a continuum rather than a series of discrete steps.

Without wishing to be bound to any particular theory, the wound healing process begins with a disturbance of blood vessel integrity that exposes the subendothelial collagen to blood platelets. This event is the initiating step that leads to blood extravasation and triggers the acute inflammatory response. This response activates local and systemic factors that lead to an orderly and predictable migration of cells into the wound. The first cells to appear in the wound are neutrophils, followed by monocytes and fibroblasts. Fibroblasts are the dominant cell type during fibroplasia. This phase is characterized by fibroblast proliferation and migration. The major function of the fibroblast during this stage is to elaborate interstitial matrix and collagen type-1. It is this collagen that makes up the fibrous tissue that characterizes the clinical entity referred to as scar tissue. When the fibroplasia stage is complete, the final stage of maturation occurs during which the wound becomes acellular and undergoes remodeling over months to years. During the remodeling phase the wound gathers tensile strength. Under the influence of various mediators and enzymes, remodeling is thought to represent the interplay between matrix synthesis and degradation.

Provided herein are compositions, devices and methods of treatment to improve wound healing after medical procedures such as surgery, or other trauma. In some embodiments, the present invention provides collagen inhibitors topically administered to the wound or site of injury. "Stenosis" or "stricture" refers to the narrowing of a bodily canal, passageway or tubular structure or organ.

"Subjects" that may be treated by the present invention include both human subjects for medical purposes and animal subjects for veterinary and laboratory purposes. Other suitable animal subjects are, in general, mammalian subjects such as primates, bovines, ovines, caprines, porcines, equines, felines, canines, lagomorphs, rodents (e.g., rats and mice), etc. Human subjects are the most preferred. Human subjects include fetal, neonatal, infant, juvenile, adult and geriatric subjects.

"Treat" as used herein refers to any type of treatment or prevention that imparts a benefit to a subject afflicted with or at risk of developing scarring or complications involving scar tissue production and/or collagen production, including improvement in the condition of the subject (e.g., in one or more symptoms), delay in the progression of the scarring, delay the onset of symptoms or slow the progression of symptoms, etc. As such, the term "treatment" also includes prophylactic treatment of the subject to prevent the onset of symptoms. As used herein, "treatment" and "prevention" are not necessarily meant to imply cure or complete abolition of symptoms, but refer to any type of treatment that imparts a benefit to a patient afflicted with a disease, including improvement in the condition of the patient (e.g., in one or more symptoms), delay in the progression of the disease, etc.

"Treatment effective amount", "amount effective to treat" or the like as used herein means an amount of the collagen inhibitor sufficient to produce a desirable effect upon a patient inflicted with wounds or site of injury. This includes improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

I. Collagen Inhibitors

"Collagen inhibitors" useful for carrying out the present invention are known and include all agents that inhibit the synthesis of collagen. See, e.g., U.S. Pat. Nos. 6,046,340 and 5,092,841; PCT Publication No. WO/2005/112999. Collagen is the major protein component of the extracellular matrix in organisms. There are at least 12 types of collagens, with types I, II and III being the most common. They are primarily synthesized in the body by fibroblasts during healing, and are formed by processing of the precursor procollagen proteins.

In some embodiments, inhibitors of type-1 collagen (also known as type I collagen) are preferred. The primary component of scar tissue, collagen type-1 alpha, typically forms a protein rod 300 nm long composed of 3 subunits: two $\alpha1(I)$ chains and one $\alpha2(I)$ chain. Within the fibroblast, elaboration of type-1 collagen is controlled by activation of the alpha-1 collagen gene. Therefore, in some embodiments, inhibitors of the alpha-1 collagen gene expression are preferred.

Examples of "collagen inhibitors" as used herein include, but are not limited to, mithramycin, mitomycin-c, tranilast, halofuginone, d-penicillamine, beta-aminopropionitrile, okadaic acid, LY294002 (PI-3K inhibitor), 5-fluorouracil, analogs thereof, etc.

Mithramycin (MIT or plicamycin) is an aureolic acid polyketide antibiotic that binds to GC-rich areas of DNA, and is typically used as a chemotherapeutic agent. See, e.g., U.S. Pat. No. 5,723,448. Mitomycin-c is a known fibroblast inhibitor with known scar inhibitory effects in the eye, sinus and trachea.

Tranilast (2-(2,3-dimethoxycinnamoyl)aminobenzoic acid) is also known and described in, for example, U.S. Pat. Nos. 5,385,935; 6,239,177; and 6,376,543.

"Halofuginone" or halofuginone bromide (7-bromo-6-chloro-3-[3-(3-hydroxy-2-piperidinyl)-2-oxopropyl]-4(3H) is known and described in, for example, U.S. Pat. Nos. 5,449,678, 6,420,371; 6,028,078; 6,090,814; and 6,159,488. Halofuginone is a quinazolinone compound that has been used in the cattle and poultry industries as an anti-coccidal agent. Serendipitously, it was discovered that dermal thinning was occurring in chickens that were administered the drug systemically. Further study of this phenomenon led to the discovery that the mechanism of action of halofuginone was inhibition of the alpha-1 collagen gene promoter (Granot I et al. Poult Sci. 1991 July; 70(7):1559-63). The pharmacology of this compound has been extensively studied for veterinary use and has FDA orphan drug approval for use in humans to treat scleroderma.

II. Substrates

Substrates include any biocompatible substrate, and may be biodegradable or non-biodegradable.

Biodegradable or bioabsorbable substrates may be formed of biodegradable polymers. Any suitable polymer may be employed, including, but not limited to, poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, as well as blends and copolymers thereof. See, e.g., U.S. Pat. No. 7,097,857.

According to some embodiments, the present invention provides a wound closure device comprising a substrate and a collagen inhibitor on or in said substrate. The substrate may comprise, consist of or consist essentially of a biodegradable substrate (such as albumin, collagen, synthetic polyamino acids, prolamines, polysaccharides, etc., or biodegradable polymers such as polylactides, polyglycolic acids, poly(lactide-co-glycolides), polycaprolactones, polycarbonates, polyamides, polyanhydrides, polyamino acids, polyortho esters, polyacetals, polycyanoacrylates, and degradable polyurethanes) or a non-biodegradable (inert) substrates such as silicone and silk, or polyvinyl alcohol, polyethylene, polyurethane, polypropylene, polycaprolactone, polyacrylates, ethylene-vinyl acetates, polystyrenes, polyvinyl oxides, polyvinyl fluorides, poly(vinyl imidazoles), chlorosulphonated polyolefins, polyethylene oxides, polytetrafluoroethylenes, nylons, and copolymers and combinations thereof. The device may take any suitable form, such as a suture, staple, tape, or bandage. In some embodiments the collagen inhibitor is carried in a biodegradable polymer which is coated on an inert or non-biodegradable substrate.

In some embodiments the device is a suture. Sutures may be formed of biodegradable polymers as described above (which may be in the form of a unitary solid), or may be formed from braided, woven, or non-woven fiber material (e.g., silk, cotton, rayon, linen, wool, satin, nylon, polyester or mixtures thereof). See, e.g., U.S. Pat. Nos. 5,685,860 and 6,224,630. In some embodiments, sutures include polypropylene (e.g., prolene or marlex) and/or polytetrafluoroethylene (PTFE) (e.g., Gore-Tex).

The present invention also provides surgical packings (e.g., sinus packings) that include a substrate and a collagen inhibitor on or in said substrate. The packing may take any suitable form, including, but not limited to, those described in U.S. Pat. Nos. 5,263,927 and 4,291,687.

The substrate material for the packing may be formed of any suitable material, including but not limited to methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, carboxymethylcellulose, microcrystalline cellulose, xanthan gum, silicon dioxide, and mixtures thereof. See, e.g., U.S. Pat. No. 7,135,197. Oxycellulose is currently used as a wound packing to achieve hemostatis. In some embodiments the substrate may be provided in the form of a dry, preferably sterile, powder (e.g., with which the collagen inhibitor may be mixed).

In some embodiments, a barrier material is used for preventing adhesions in a subject, comprising in combination, a preformed or in situ formable barrier substrate and a collagen inhibitor on or in said substrate. The substrate may be any suitable material, and when formed in situ any suitable crosslinking agent may be employed. Suitable examples include but are not limited to those described in U.S. Pat. No. 6,638,917. The substrate or material may be bioabsorbable (e.g., a hemostatic material) or non-bioabsorbable (e.g., a non-absorbable mesh, such as is currently used in hernia repair).

A further aspect of the invention is an implantable or insertable biomedical device comprising a substrate and a collagen inhibitor on or in said substrate. In some embodiments, the device is a urethral, ureteral, or nephroureteral catheter or stent. Various nasal, esophageal and tracheal stents are also known. Cranial, maxillary and mandibular bone plates include bioabsorbable substrates (such as poly-L-lactic-polyglycolic plates (PLLA/PGA)) and non-bioabsorbable substrates (such as titanium).

In some embodiments, a non-bioabsorbable stent (i.e., a tube designed to prevent luminal strictures) anywhere in the body. Examples include, but are not limited to, Urethral catheter, Ureteral stent, Nephroureteral catheter, Esophageal stent, Tracheostomy stent, Gastric feeding tube, Nasogastric tube, Laryngeal/tracheal/pulmonary stent, Myringotomy tube, Nasal stent, Salivary duct stent, Biliary stent, Enteric stents, Nasolacrimal stents.

Still other examples are described below. The substrate may be comprised of any suitable biodegradable or non-biodegradable material. In some embodiments the substrate (e.g., from which the catheter is formed) comprises a material such as vinyl, polyethylene, poly(vinyl chloride) (PVC), ethylene vinyl acetate (EVA), silicone, latex, or polypropylene. See, e.g., U.S. Pat. No. 7,025,753. The collagen inhibitor may be coated on such a substrate material, with or without a carrier (such as a biodegradable polymer), by any suitable technique as discussed further below.

Specific examples of devices or products that can be used to carry out the present invention by including a collagen inhibitor on or in a substrate from which the product or device is formed include, but are not limited to (for various fields):

Urology:
Coated Urethral Catheter
Coated Ureteral Stent
Coated Nephroureteral Catheter
ENT:
Coated Sinus Packing Material
Injectable sinus packing material
Coated Esophageal Stent
Coated Tracheostomy Tube
Coated Gastric Feeding Tube
Coated Nasogastric Tube
Coated Laryngeal/Tracheal/Pulmonary Stent
Injectable Material for Vocal Fold Augmentation
Coated Myringotomy Tube
Coated Nasal Septal Splint
Coated Nasal Stent
Coated Salivary Duct Stent
Coated Laryngeal Implant
Injectable gel for salivary radiation fibrosis
Coated cranial, maxillary, mandibular absorbable and non-absorbable bone plates
Plastic Surgery/Dermatology:
Coated Silicone Implants (or Coated Implants of other Composition)
Injectable Material for Cosmetic Augmentation (Bulking Agent)
Cream/Gel/Spray for Prevention of Hypertrophic Scar
Coated Silicone Sheets for the Prevention of Scarring
Cream/Gel/Spray/Silicone Sheets to Prevent Burn Scarring/Contractures
Coated skin graft material
Coated Suture for Wound Closure
Coated Skin Staples/Intracorporeal Staples
Coated "Steri-Strips" Wound Closure Adhesives
General Surgery:
Coated Sheets or Sprays for the Prevention of Surgical Adhesions
Coated Biliary Stents
Coated Enteric Stents
Ophthalmology
Coated Nasolacmmal Stents
Vascular Surgery:
Coated Endovascular Stents
Cardiology:
Coated Endovascular Cardiac Stents
Orthopaedic:
Coated absorbable and nonabsorbable bone plates
Miscellaneous:
Coating for other Implanted Artificial Medical Devices (vascular access devices, insulin pumps, etc)
Coated synthetic polymers [e.g., polyglycolic acid (PGA), polylactic acid (PLA), and poly(lactic-co-glycolic acid) (PLGA)], used to make absorbable vascular stent, cardiovascular stents, staples, suture Devices, materials, and compositions of the invention may be used in the treatment of both human subjects and animal subjects such as dogs, cats, horses, cattle, sheep, monkeys, etc. for veterinary or laboratory purposes.

Kits are also provided, wherein the coated substrate is provided in a suitable package ready for use.

III. Formulations

In some embodiments, collagen inhibitors of the present invention are provided as a coating on a substrate. Collagen inhibitors may be coated on a substrate by any suitable technique, such as dipping, spraying, spray drying, etc. The collagen inhibitor may be applied per se or concurrently with a carrier material or film-forming material, such as a biodegradable polymer (e.g., as described above). Collagen inhibitors may be combined into materials (such as powders or biodegradable materials) by any suitable technique, such as mixing, co-extruding, etc. In some embodiments, the collagen inhibitor is included in an amount effective to inhibit scar formation and/or collagen formation on or adjacent the implanted or inserted substrate.

According to some embodiments, for suture and/or packing materials the coating process includes one or more of the following steps: (a) prepare materials to desired size and shape for implantation; (b) prepare a solution of a collagen inhibitor (e.g., HFBr at 0.5 µg/ml); (c) materials are then dipped and immediately frozen at −80 F for approximately 24 hours; (d) Frozen materials are then lyophilized (i.e., vacuum dried); (e) materials are sterilized, e.g., using ethylene oxide or gamma irradiation.

According to some embodiments, coating and/or impregnating stent materials (e.g., for esophagus, trachea, vascular, etc.) with a collagen inhibitor includes one or more of the following steps: (a) dry collagen inhibitor (e.g., HFBr) in powder form is mixed (e.g., in a 50:50 ratio) with stent material also in powder form (e.g., PLLA, PGA, Vicryl (polygalactin)); (b) powder material is then electrospun into desired shape (in some embodiments, this process results in a collagen inhibitor impregnated stent that allows freedom to make the desired shape for implantation); (c) stent is sterilized, e.g., using ethylene oxide or gamma irradiation.

According to some embodiments, wound glue including a collagen inhibitor includes one or more of the following steps: (a) the collagen inhibitor (e.g., HFBr at 0.5 µg/ml) is mixed 50:50 with a suitable glue material (e.g., acrylate material); and (b) applied directly to the wound.

According to some embodiments, coating of stents (e.g., permanent catheters) with a collagen inhibitor includes one or more of the following steps. (a) Weigh stent; (b) Modify surface of the stent with a plasma reactor, or alternatively microwave water wet stent for about 30-60 seconds; (c) Imerse stent in collagen inhibitor (e.g., halofuginone) and freeze in liquid nitrogen or −80 C); (d) Lyophilize stent (e.g., overnight); (e) Weigh stent; (f) Immerse stent in 1% PEG (3500-5000 g/mol filtered in 0.2 um filter); (g) Freeze PEG in liquid nitrogen or −80 C, and lyophilize overnight; (h) Immerse stent in collagen inhibitor (e.g., halofuginone) and freeze and lyophilize overnight; (i) Weigh stent; and (j) Sterilize.

According to some embodiments, coating of stents (e.g., permanent catheters) with a collagen inhibitor includes one or more of the following steps. (a) Weigh stent (b) Modify surface of the stent with a plasma reactor, or alternatively microwave wet stent (e.g., wet with PBS and covered with PBS soaked gauze) for about 30-60 seconds; (c) Dip stent in 2% PLGA-COOH to cool; (d) Dry under hood; (e) Cover with soaked gauze (e.g., with PBS) and microwave for about 30-60 seconds (or use plasma reactor); (f) Coat stent with halofuginone (e.g., immerse) and freeze in liquid nitrogen and lyophilize overnight; (g) Weight stent to estimate drug content; and (h) Sterilize.

Those of skill in the art will appreciate that all of the above methods can be modified and optimized as desired by routine methods without departing from the spirit of the invention disclosed herein.

IV. Dosages and Routes of Administration

In preferred embodiments, collagen inhibitors of the present invention are administered topically (i.e., locally) to the wound or site of injury. In some embodiments, compositions including collagen inhibitors may be administered via a coated suture, via combination with a gel or suitable wound glue, via coatings and/or impregnating collagen inhibitors onto a suitable substrate as described herein.

In some embodiments, topical application of one or more collagen inhibitors in nano ($10^{-9}$) or pico ($10^{-12}$) molar doses is sufficient to inhibit collagen type-1 production in an open wound. In some embodiments, collagen inhibitors is used topically as a packing material (e.g., in the sinus after paranasal sinus surgery) to prevent post-operative scar tissue formation.

In some embodiments, collagen inhibitors are administered by elution/absorption of the drug in less than 30 minutes. In some embodiments, administration is performed over a longer period of time, e.g., substantial elution over 30 minutes, 1, 2 or 3 hours, and up to 5, 6, 7 or 8 days. In some embodiments, collagen inhibitors are eluted over time to capture as much of the early fibroplasia stage of wound healing as possible (e.g., over 3-7 days).

In some embodiments, HF is administered in a single or total dosage over time of 0.5, 1.0 or 1.5 to 2.0, 2.5, 3.0, 3.5 or 4.0 mg/kg. In some embodiments, the total dosage is 0.5 to 10 mg. In some embodiments, HF is administered in nano ($10^{-9}$) or pico ($10^{-12}$) molar doses.

Some embodiments of present invention are explained in greater detail in the following non-limiting examples.

EXAMPLES

Example 1

Coated Ureteral and Urethral Catheter Material

A collagen inhibitor coated catheter could be inserted following stricture incision, preventing recurrence by delivering a small amount of collagen inhibitor to the specific area of interest.

Halofuginone bromide (HF) is a substance known to be a potent Collagen Type I inhibiter, and previous studies have demonstrated that oral and local halofuginone administration can prevent luminal strictures, including urethral strictures. However, no previous studies have demonstrated the ability of HF coated stents to prevent urethral stricture formation. The objectives of this study were to successfully coat urethral stents with HF, and then to test whether HF coated stents could prevent spongiofibrosis in a small animal model of urethral stricture disease.

Halocur® (Oral Halofuginone. 0.5 mg/mL) was obtained from Intervet International BV of Norway. The rat stents were made of silicone tubing (0.30 mm×0.64 mm) from SMI, while the rabbit stents were 8fr silicone Foley catheters (Bard). The stents were coated as follows: 1. Wet stent with PBS and cover with PBS soaked gauze and microwave for 40 sec; 2. Dip stent in 2% PLGA-COOH to cool; 3. Dry under hood; 4. Cover with PBS soaked gauze and microwave (or plasma) for 30 sec; 5. Coat stent with halofuginone (immerse) and freeze in liquid nitrogen and lyophilize overnight; 6. Weight should be measured before and after coating to estimate drug content. The presence of halofuginone on the catheters was documented by measuring changes in stent weight, gross and SEM imaging studies, and elution kinetics.

The simplest method of measuring drug coating, namely determinations of changes in weight, was performed first. Silicone tubing of 3 cm in length was weighed before and after coating with Halocur. The average weight change following coating was approximately 1 mg, demonstrating the coating of a small amount of drug on the tubing. Visual inspection of the coated catheters also demonstrated a yellow coating over the usual white appearance of the silicone, providing further evidence that the yellow Halocur had adhered to the tubing.

Scanning electron microscopy of the silicone tubing was also performed before and after coating with Halocur (FIG. 1). The coated tube clearly demonstrates a layer of drug on its surface, while the uncoated tube is completely smooth. This provides further evidence that the Halocur was successfully coated on the silicone tubing.

Figure 5:
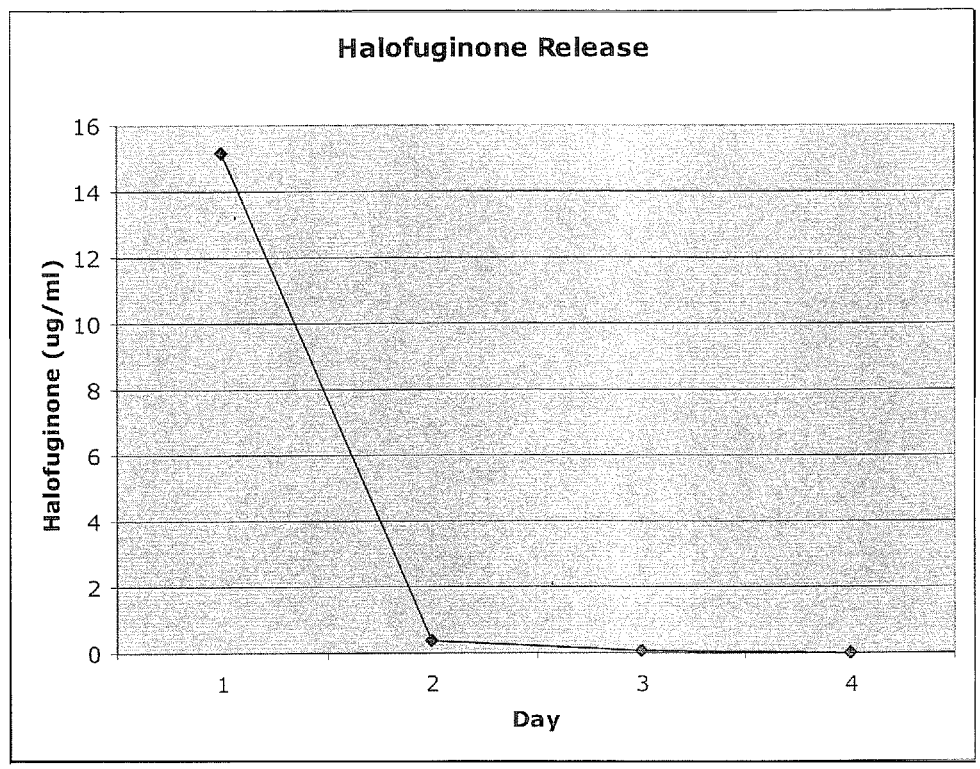
FIG. 5. HF Elution.

Drug release studies were then performed to determine the amount of halofuginone released by the coated stents, and the timing of drug release. Stents approximately 3 cm in length were coated with halofuginone using our proprietary technique. These stents were then placed in PBS solution at room temperature for 24-hour intervals. After each 24-hour interval, the stents were placed in a new PBS solution, and the previous solution was analyzed for halofuginone concentration using UV spectroscopy (absorption at 243 nm). This process was continued daily until the amount of halofuginone in the PBS dropped to immeasurable levels. There was a sustained release of halofuginone from the stents for approximately 4 days, with a large burst release the first 24 hours, and progressively less the following 3 days (FIG. 5). These results provided further evidence that the silicone stents had been successfully coated with Halocur, and that this coating provided a sustained release of drug over a several day period.

Animal Surgeries (Rat and Rabbit): Urethral scars were formed in the urethra via electrocautery using an established animal model (Jaidane et al. *J. Urol.* 2003 November 170(5): 2049-52). Uncoated (control) or HF-coated (experimental) stent was inserted into the urethrae and secured with permanent sutures. The rabbits had perineal urethrostomies. The rats were euthanized at 2 weeks and the rabbits at 3 months post-surgery, at which point the penes (containing the urethral stents) and surrounding subcutaneous tissues were excised.

The specimens were fixed in 10% paraformalin and embedded in paraffin blocks. The specimen was then sectioned (5 µm), made into slides, and stained with Masson's trichrome and alpha 1 collagen antibody staining.

HF Analysis in Local Tissues and Serum (in Rat): The tissue specimens were morcellated, incubated for 24 hours in 40 mL of PBS, centrifuged, and a sample was taken for HF concentration analysis via spectrophotometry. Blood was also drawn (1 mL) from the heart post-mortem, added to 5 mL of PBS, centrifuged, and the serum analyzed for HF concentration via spectrophotometry.

Figure 2:
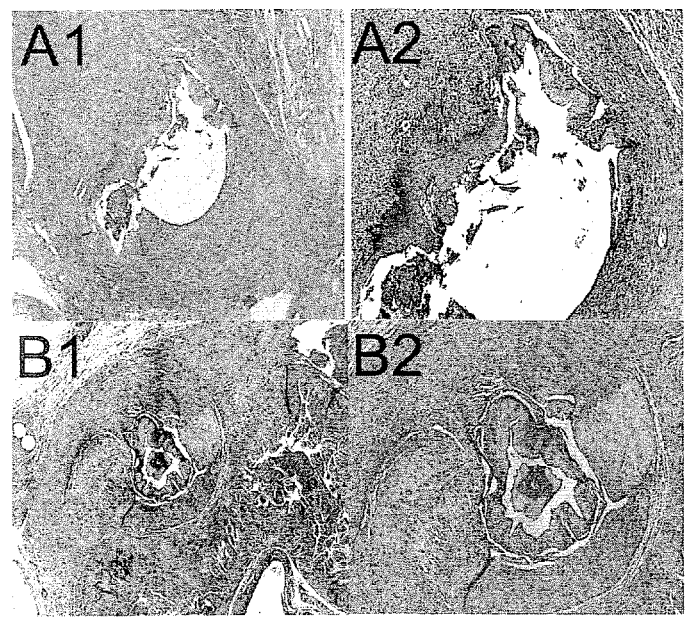
FIG. 2. Masson's Trichlome Stain of 2-Week Rat Urethra. A: Samples had HF-coated stent. B: Samples had uncoated stent. In slides A1 (2.5×) and A2 (10×), there is no new collagen deposition (no spongiofibrosis), but only an inflammatory response. In slides B1 (2.5×) and B2 (10×), there is obvious new collagen deposition (spongiofibrosis).
Figure 3:
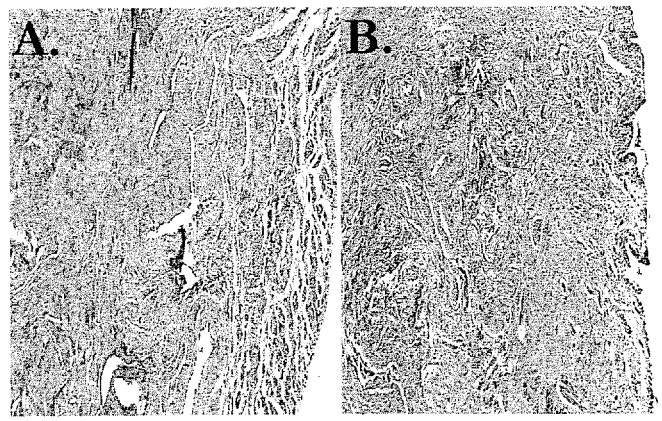
FIG. 3. Masson's Trichrome Stain of 3-month Rabbit Urethra. A: Sample had HF-coated stent. B: Sample had uncoated stent. In slide A, there is less collagen deposition (less blue stain) with normal urethral architecture. In slide B, there is greater collagen deposition (more blue stain), but note that at 3 months the collagen has become more organized, unlike the amorphous collagen seen at 2 weeks.
Figure 4:
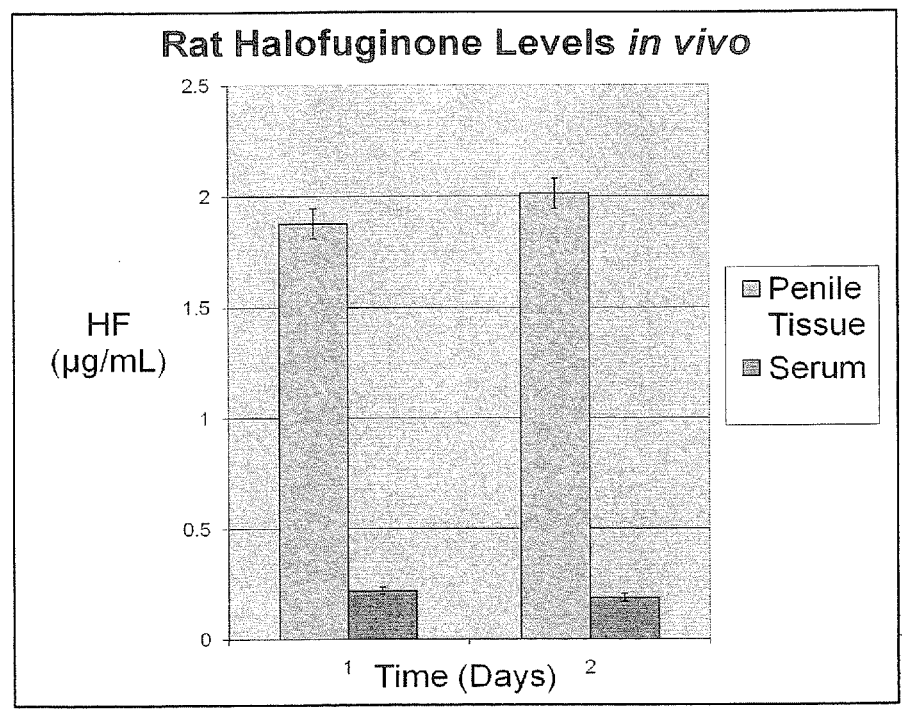
FIG. 4. Rat Halofuginone Levels in vivo. The concentration of HF was determined in both the penile tissue and blood serum. There is almost a ten-fold difference between HF levels in the serum vs. the penile tissue. Standard error bars are included.

Results: The silicone stents were successfully coated with halofuginone. Scars were effectively induced in both animal models, utilizing the electrocautery technique, and scar formation was characterized by increased collagen deposition within damaged tissues (see FIG. 2 and FIG. 3). On gross examination, there was obvious collagen deposition (spongiofibrosis) seen in the penes with the uncoated stents, while there was no new collagen deposition in the spongiosal tissue of the penes with the HF-coated stent. This result was observed in both the rat and rabbit animal model (FIG. 2 and FIG. 3, respectively). HF was detected in both the surrounding penile tissues and in the bloodstream serum, but the level of HF was significantly higher in the tissues than in the serum (FIG. 4).

Conclusions: HF coated stents resulted in no new periurethral collagen deposition in response to injury, thereby causing less scarring of the insulted area. This may correlate to reduced stricture formation. HF is present in both tissues adjacent to the drug-eluting stent and in the blood serum, and significantly higher concentrations are seen in local tissues than in the blood serum.

Example 2

Human Testing

Ten male patients with comparable urethral strictures amenable to treatment by DVIU therapy (<2 cm length) are recruited and divided into 2 treatment groups. Group A (5 men) are treated with DVIU and then stented for 4 days with a silicone urethral Foley catheter. Group B (5 men) are treated with DVIU and then stented for 4 days with a type-I collagen inhibitor coated silicone catheter.

The type-I collagen inhibitor coated silicone urethral catheter consists of a Bard All-Silicone 16 french Foley catheter (already in widespread use in humans), coated with the specific type-I collagen inhibitor halofuginone, approximately 0.375 mg of halofuginone in the form of the solution Halocur. The catheters used will be Bard 16 french 100% silicone Foley catheters, purchased for hospital use through the usual vendors, and therefore packaged sterilely. The catheter will then be removed from its packaging and coated with the drug Halocur (0.5 mg/ml halofuginone solution) as described above. The Halocur is obtained from the Intervet Corporation, which produces Halocur in large quantities with excellent quality control for use in the treatment of Crytosporidium parvum in newborn calves. Once the catheter is coated, it is packaged and sterilized under UV or gamma irradiation in preparation for patient use.

Immediately following removal of the catheter (and then every 3 months for a year), the patients undergo uroflowmetry evaluation in the standard fashion. At the end of the year, all patients undergo a retrograde urethrogram to evaluate urethral patency.

Qualitatively, the safety of the type-I collagen inhibitor coated catheter is assessed, as patients are observed for any untoward effects from the use of the stent. Quantitatively, recurrence of the urethral stricture is assessed by measuring uroflow rates as well as urethral caliber on retrograde urethrograms. The uroflowmetry results will be objectively compared by measuring the maximal flow rate (or Qmax), and subjectively compared by analyzing the shape of the flow curve (unimodal with normal monotonic increase, stable period, and monotonic decrease signifying normal flow, versus a multimodal extended pattern signifying obstructed flow). The retrograde urethrography studies will be objectively compared by measuring the urethral width at its most narrow point to evaluate for stricture recurrence in each case.

Example 3

Catheter Coating

The following is a list of ureteral and urethral catheter material that we have demonstrated the ability to coat with halofuginone using imaging studies (microscopic and gross), weight changes, and elution data over 4 days:

General device material: Silicone, Silastic, Latex, Polyurethane, Nitinol, PLGA.

Boston Scientific products: Percuflex stents, Flexima stents, Pebax material.

Cook stents: Polyurethane, Sof-flex, AQ stents, Endo-sof stents.

Bard stents: Polyurethane, Latex, Woven stents, Lubricath Foley, Inlay stent, Elastomer coated catheters, Silver coated catheters.

The stents were coated as follows: 1. Wet stent with PBS and cover with PBS soaked gauze and microwave for 40 sec; 2. Dip stent in 2% PLGA-COOH to cool; 3. Dry under hood; 4. Cover with PBS soaked gauze and microwave (or plasma) for 30 sec; 5. Coat stent with halofuginone (immerse) and freeze in liquid nitrogen and lyophilize overnight; 6. Weight should be measured before and after coating to estimate drug content.

The foregoing is illustrative of the present invention, and is not to be construed as limiting thereof. The invention is defined by the following claims, with equivalents of the claims to be included therein.

That which is claimed is:

1. A non-bioabsorbable urethral, ureteral or nephroureteral stent or catheter comprising a substrate and halofuginone on or in said substrate, said halofuginone provided on or in said stent or catheter in an amount effective to inhibit spongiofibrosis, wherein said stent or catheter has substantial elution of said halofuginone over a period of up to 8 days.

2. The stent or catheter of claim 1, wherein said substrate is comprised of a material selected from the group consisting of vinyl, polyethylene, poly(vinyl chloride) (PVC), ethylene vinyl acetate (EVA), silicone, latex, and polypropylene.

3. A method of treating urethral or ureteral strictures in a subject in need thereof comprising topically administering a collagen inhibitor in an amount effective to treat said strictures in said subject,
wherein said administering step is carried out by stenting said strictures with the stent or catheter of claim 1.

4. The method of claim 3, wherein said stenting is carried out following stricture incision in said subject.

5. The method of claim 3, wherein said stent or catheter comprises silicone.

6. The method of claim 3, wherein said stent or catheter releases said collagen inhibitor for a time of from 1 to 4 days.

7. A kit comprising:
(a) a non-bioabsorbable substrate coated with halofuginone, said halofuginone provided on or in said substrate in an amount effective to inhibit spongiofibrosis, wherein said substrate has substantial elution of said halofuginone over a period of up to 8 days; and
(b) a container in which said substrate is packaged in sterile form,
wherein said substrate is a urethral, ureteral, or nephroureteral catheter or stent.

8. The kit of claim 7, wherein said container comprises a plastic or foil container.

9. The kit of claim 7, wherein said container is vacuum-packed.

10. The kit of claim 7, wherein said substrate is coated with a single unit dose of said collagen inhibitor.

11. The kit of claim 7, wherein said substrate is comprised of a material selected from the group consisting of vinyl, polyethylene, poly(vinyl chloride) (PVC), ethylene vinyl acetate (EVA), silicone, latex, and polypropylene.

12. A non-bioabsorbable stent comprising a substrate and halofuginone on or in said substrate,
wherein said stent is a urethral, ureteral, or nephroureteral stent,
wherein said halofuginone is provided on or in said stent or catheter in an amount effective to inhibit spongiofibrosis, wherein said stent or catheter has substantial elution of said halofuginone over a period of up to 8 days, and
wherein said substrate is comprised of a material selected from the group consisting of vinyl, polyethylene, poly(vinyl chloride) (PVC), ethylene vinyl acetate (EVA), silicone, latex, and polypropylene.

13. A kit comprising:
(a) The stent of claim 12; and
(b) a container in which said substrate is packaged in sterile form.

14. The kit of claim 13, wherein said container comprises a plastic or foil container.

15. The kit of claim 13, wherein said container is vacuum-packed.

16. The kit of claim 13, wherein said substrate is coated with a single unit dose of said collagen inhibitor.

17. The stent or catheter of claim 1, wherein said substrate is comprised of a material selected from the group consisting of silicone and polyurethane.

18. The stent or catheter of claim 1, wherein said stent or catheter is removable.

* * * * *